United States Patent [19]

Eicken et al.

[11] Patent Number: 4,498,922
[45] Date of Patent: Feb. 12, 1985

[54] N-AMINOMETHYLHALOACETANILIDES AND THEIR USE FOR CONTROLLING UNDESIRABLE PLANT GROWTH

[75] Inventors: Karl Eicken; Wolfgang Rohr, both of Wachenheim; Bruno Wuerzer, Otterstadt, all of Fed. Rep. of Germany

[73] Assignee: BASF Aktiengesellschaft, Fed. Rep. of Germany

[21] Appl. No.: 401,355

[22] Filed: Jul. 23, 1982

[30] Foreign Application Priority Data

Jul. 31, 1981 [DE] Fed. Rep. of Germany ....... 3130302

[51] Int. Cl.³ .................. C07C 125/065; A01N 37/22
[52] U.S. Cl. ........................................ 71/111; 560/30; 260/465 D; 71/105
[58] Field of Search ..................... 560/30; 260/465 D; 71/105, 111

[56] References Cited

U.S. PATENT DOCUMENTS

| | | | |
|---|---|---|---|
| 3,442,945 | 5/1969 | Olin | 260/562 |
| 3,769,301 | 10/1973 | Olin | 260/326.45 |
| 3,901,685 | 8/1975 | Ratts | 71/118 |
| 3,937,730 | 2/1976 | Vogel et al. | |
| 4,097,262 | 6/1978 | Cheng | 71/90 |
| 4,235,928 | 11/1980 | Eicken et al. | 424/300 |

FOREIGN PATENT DOCUMENTS 33114 1/1981 European Pat. Off.

Primary Examiner—Bernard Helfin
Attorney, Agent, or Firm—Keil & Weinkauf

[57] ABSTRACT

Substituted N-aminomethylhaloacetanilides of the formula

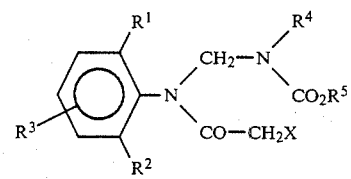

where $R^1$ and $R^2$ are each $C_1$–$C_2$-alkyl, $R^3$ is hydrogen or $C_1$–$C_4$-alkyl, $R^4$ is cyano or —CO—$NH_2$, $R^5$ is $C_1$–$C_6$-alkyl and X is halogen, are used for controlling undesirable plant growth.

6 Claims, No Drawings

N-AMINOMETHYLHALOACETANILIDES AND THEIR USE FOR CONTROLLING UNDESIRABLE PLANT GROWTH

The present invention relates to N-aminomethylhaloacetanilides, herbicides containing these compounds as active ingredients, and a process for controlling undesirable plant growth with these compounds.

It has been disclosed that 2,6-diethyl-N-methoxymethyl-2'-chloroacetanilide (U.S. Pat. No. 3,442,945) and 2-methyl-6-ethyl-N-(2-methoxy-1-methylethyl)-2'-chloroacetanilide (German Laid-Open Application DOS No. 2,328,340), inter alia, are herbicidal haloacetanilides. Moreover, it has been disclosed that chloroacetanilides possessing amide groups bonded via methylene exhibit a herbicidal action (German Laid-Open Laid Application DOS No. 2,226,593, and U.S. Pat. Nos. 4,097,262 and 3,901,685).

We have found that substituted N-aminomethylhaloacetanilides of the formula

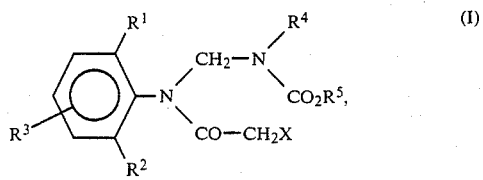

where $R^1$ and $R^2$ are each $C_1$–$C_2$-alkyl, $R^3$ is hydrogen or $C_1$–$C_4$-alkyl, $R^4$ is cyano or —CO—NH$_2$, $R^5$ is $C_1$14 $C_6$-alkyl and X is halogen, are particularly well tolerated by crop plants and exhibit good herbicidal activity.

For the purposes of the invention, $R^1$, $R^2$, $R^3$ and $R^5$ are each, for example, one of the following radicals, depending on the number of carbon atoms stated: methyl, ethyl, n-propyl, iso-propyl, n-butyl, iso-butyl, sec.-butyl, tert.-butyl, n-pentyl or n-hexyl, or an isomer of one of these. X is chlorine, bromine or iodine. $R^4$ is preferably —CO—NH$_2$, and X is preferably chlorine.

The substituted N-aminomethylhaloacetanilides wherein $R^4$ is cyano are obtained by reacting an N-halomethylhaloacetanilide of the formula

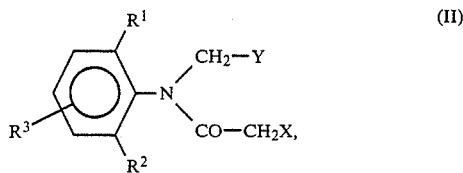

where $R^1$, $R^2$, $R^3$ and X have the above meaning, and Y is halogen, eg. chlorine, bromine or iodine, with a cyanamide of the formula

where $R^5$ has the above meaning, and M is hydrogen, an alkali metal or tetraalkylammonium, in the presence or absence of an acid acceptor and in the presence or absence of a solvent which is inert to the reactants.

Examples of suitable solvents are aromatic hydrocarbons, eg. toluene and xylene, haloaliphatic or haloaromatic hydrocarbons, eg. chlorobenzene, chloroform or methylene chloride, ethers, eg. tetrahydrofuran, nitriles, eg. acetonitrile, N,N-dialkylamides, eg. dimethylformamide, and sulfones, eg. dimethylsulfoxide, as well as mixtures of these. The reaction is carried out at from 0° to 150° C., preferably from 20° to 100° C.

If a cyanamide of the formula III where M is hydrogen is reacted, it is advisable to use an acid acceptor. Examples of suitable acid acceptors are tertiary amines, eg. triethylamine, pyridine and substituted pyridines, and inorganic bases, eg. oxides, hydroxides, carbonates and bicarbonates of alkali metals.

Not less than 1 mole, for example from 1 to 1.2 moles, of the cyanamide of the formula III is employed per mole of the N-halomethylhaloacetanilide of the formula II. To isolate the compound of the formula I where $R^4$ is cyano, for example, the halide formed is filtered off if necessary, the filtrate is then evaporated down, and the residue is dissolved in an organic, water-immiscible solvent. Thereafter, the organic phase is washed with water, dried, and concentrated under reduced pressure. In many cases, the end product obtained is pure, but, if necessary, it may be purified by recrystallization or by chromatography over silica gel.

Some of the N-halomethylhaloacetanilides used as starting compounds are known (German Published Application DAS No. 1,542,950). They may be prepared in a conventional manner, by reacting an appropriately substituted phenylazomethine with a haloacetyl halide.

Cyanamides of the formula III are likewise known (German Laid-Open Applications DOS No. 2,474,453 and DOS No. 1,795,849).

Specific examples of cyanamides which are suitable starting materials, and of salts of these compounds, are methyl cyanocarbamate, ethyl cyanocarbamate and n-propyl cyanocarbamate, and their sodium, potassium and tetramethylammonium salts, and isopropyl cyanocarbamate, n-butyl cyanocarbamate, sec.-butyl cyanocarbamate, and n-hexyl cyanocarbamate, and their sodium and potassium salts.

N-Aminomethyl-haloacetanilides wherein $R^4$ is —CO—NH$_2$ are obtained by reacting the corresponding compound wherein $R^4$ is cyano with a mineral acid, in the presence of an alcohol, and hydrolyzing the product in the presence or absence of an inert diluent. The reaction may be carried out in a diluent which is inert to the reactants, examples of suitable diluents being aromatic hydrocarbons, eg. toluene and xylene, haloaliphatic or haloaromatic hydrocarbons, eg. chlorobenzene, chloroform and methylene chloride, and ethers, eg. diethyl ether and tetrahydrofuran, as well as mixtures of these solvents. The reaction is carried out at from −30° to +100° C., preferably from −10° to +30° C. Preferred mineral acids are hydrohalic acids, eg. hydrochloric acid and hydrobromic acid, and sulfuric acid. Preferred alcohols are lower aliphatic alcohols, eg. methanol, ethanol, n-propanol, i-propanol and butanols. The mineral acid and the alcohol are employed in not less than the stoichiometric amounts, based on the starting compound of the formula I where $R^4$ is cyano, but from 1 to 20 times the stoichiometric amounts are used in most cases. After reaction times of from 4 to 48 hours, the reaction mixture is mixed with water. The inert diluent is evaporated if necessary, and the N-aminomethylhaloacetanilide of the formula I where $R^4$ is —CO—NH$_2$ is isolated from the organic phase. This product is obtained in pure form in many cases, but it may be purified, if necessary, for example by recrystallization.

The Examples which follow illustrate the preparation of the N-aminomethylhaloacetanilides of the formula I.

EXAMPLE 1

A mixture of 52.0 g of 2'-methyl-6'-ethyl-N-chloromethyl-2-chloroacetanilide, 29.2 g of the sodium salt of methyl cyanocarbamate and 0.5 g of benzyltriethylammonium chloride in 170 ml of methylene chloride was stirred for 14 hours at 25° C. The organic phase was washed with 200 ml of water and dried, the solvent was evaporated, the residue was kneaded with a small amount of ether, and 46.5 g of N-methoxycarbonyl-N-[N'-(2-chloroacetyl)-2'-methyl-6'-ethylanilinomethyl]-cyanamide of melting point 71°–73° C. were obtained (Compound No. 1).

| $C_{15}H_{18}N_3O_3Cl$ M 325.5 | | | |
|---|---|---|---|
| | C | H | N |
| calculated: | 55.64 | 5.60 | 12.98 |
| found: | 55.8 | 6.00 | 12.6 |

EXAMPLE 2

Hydrogen chloride gas was passed into a solution of 32.4 g of N-methoxycarbonyl-N-[N'-(2-chloroacetyl)-2'-methyl-6'-ethylanilinomethyl]-cyanamide in 19.2 g of methanol and 200 ml of methylene chloride at from 0° to 5° C. until the solution was saturated. This took about 2 hours. The reaction mixture was left to stand in a closed vessel for 20 hours at the same temperature, after which 100 ml of water were added, and the mixture was then stirred for one hour at 25° C. The organic phase was washed with water, with sodium bicarbonate solution and again with water, the product was recrystallized from methanol, and 24.2 g of 2-chloro-2'-methyl-6'-ethyl-N-(N'-methoxycarbonylureidomethyl)-acetanilide of melting point 139°–141° C. were obtained (Compound No. 2).

| $C_{15}H_{20}N_3O_4Cl$ M 341.5 | | | |
|---|---|---|---|
| | C | H | N |
| calculated: | 52.71 | 5.90 | 12.29 |
| found: | 53.2 | 6.0 | 12.4 |

The following compounds of the formula I, for example, were obtained in a corresponding manner:

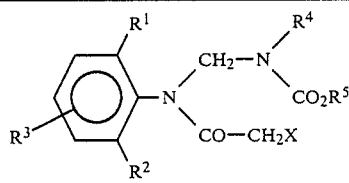

| No. | $R^1$ | $R^2$ | $R^3$ | $R^4$ | $R^5$ | X | Mp. [°C.] |
|---|---|---|---|---|---|---|---|
| 3 | CH₃ | CH₃ | H | CN | CH₃ | Cl | 125–128 |
| 5 | CH₃ | CH₃ | H | CO—NH₂ | CH₃ | Cl | 178–180 |
| 7 | CH₃ | CH₃ | H | CN | C₂H₅ | Cl | 93–95 |
| 8 | CH₃ | CH₃ | H | CO—NH₂ | C₂H₅ | Cl | 181–183 |
| 11 | CH₃ | C₂H₅ | H | CN | C₂H₅ | Cl | oil |
| 17 | C₂H₅ | C₂H₅ | H | CN | CH₃ | Cl | 78–80 |

| No. | $R^1$ | $R^2$ | $R^3$ | $R^4$ | $R^5$ | X | Mp. [°C.] |
|---|---|---|---|---|---|---|---|
| 18 | C₂H₅ | C₂H₅ | H | CO—NH₂ | CH₃ | Cl | 151–153 |

For instance the following compounds of the formula I may be obtained analogously:

| No. | $R^1$ | $R^2$ | $R^3$ | $R^4$ | $R^5$ | X |
|---|---|---|---|---|---|---|
| 4 | CH₃ | CH₃ | 3-CH₃ | CN | CH₃ | Cl |
| 6 | CH₃ | CH₃ | 3-CH₃ | CO—NH₂ | CH₃ | Cl |
| 9 | CH₃ | CH₃ | H | CO—NH₂ | CH₃ | Br |
| 10 | CH₃ | CH₃ | H | CO—NH₂ | n-C₃H₇ | Cl |
| 12 | CH₃ | C₂H₅ | H | CO—NH₂ | C₂H₅ | Cl |
| 13 | CH₃ | C₂H₅ | H | CO—NH₂ | CH₃ | Br |
| 14 | CH₃ | C₂H₅ | H | CN | n-C₃H₇ | Cl |
| 15 | CH₃ | C₂H₅ | H | CO—NH₂ | n-C₃H₇ | Cl |
| 16 | CH₃ | C₂H₅ | H | CO—NH₂ | i-C₃H₇ | Cl |
| 19 | C₂H₅ | C₂H₅ | H | CN | C₂H₅ | Cl |
| 20 | C₂H₅ | C₂H₅ | H | CO—NH₂ | C₂H₅ | Cl |

Application of the active ingredients of the formula I may be effected for instance in the form of directly sprayable solutions, powders, suspensions, dispersions, emulsions, oil dispersions, pastes, dusts, broadcasting agents, or granules by spraying, atomizing dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable. The salts may be used in the form of aqueous solutions.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g. coated, impregnated or homogeneous granules, may be prepared by bonding the active ingredients to solid carriers. Examples of solid carriers are mineral earths such as silicic acid, silica gels, silicates, talc, kaolin, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient of the formula I.

Examples of formulations are given below:

I. 20 parts of compound 18 is intimately mixed with 12 parts of the calcium salt of dodecylbenzenesufonic acid, 8 parts of a fatty alcohol polyglycol ether, 2 parts of the sodium salt of a phenolsulfonic acid-urea-formaldhyde condensate and 68 parts of a paraffinic mineral oil. A stable oily dispersion is obtained.

II. 3 parts by weight of compound 2 is intimately mixed with 97 parts by weight of particulate kaolin. A dust is obtained containing 3% by weight of the active ingredient.

III. 30 parts by weight of compound 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

IV. 40 parts by weight of compound 5 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion.

V. 20 parts by weight of compound 18 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained.

VI. 20 parts by weight of compound 3 is dissolved in a mixture consisting of 25 parts by weight of cyclohexanone, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained.

VII. 20 parts by weight of compound 1 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained.

The active ingredients, or formulations containing them, may be applied pre- or postemergence. Preferably, the novel active ingredients are applied before emergence of the unwanted plants, both on cropland and uncropped land. If certain crop plants tolerate, on leaf treatment, the active ingredients less well, application techniques may be used in which the herbicidal agents are sprayed from suitable equipment in such a manner that the leaves of sensitive crop plants are if possible not touched, and the agents reach the soil or the unwanted plants growth beneath the crop plants (post-directed, lay-by treatment).

The amount of active ingredient applied depends on the time of the year and the growth stage of the plants, and varies from 0.1 to 15 kg/ha and more, but is preferably from 0.25 to 3 kg/ha.

The influence of representatives of compounds of the formula I on the growth of unwanted and crop plants is demonstrated in greenhouse experiments and experiments in the open.

GREENHOUSE EXPERIMENTS

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as a vehicle, and sprayed through finely distributing nozzles. The application rate was equivalent to 1.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

The prior art herbicide

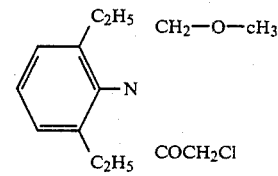

(A; U.S. Pat. No. 3,442,945) was employed for comparison purposes, also at a rate of 1.0 kg/ha.

The pots were set up in the greenhouse—species from warmer areas at from 20° to 35° C., and species from moderate climates at 10° to 25° C. The experiments were run from 2 to 4 weeks. During this period, the plants were tended and their reactions to the various treatments assessed. The scale used for assessment was 0 to 100, 0 denoting no damage or normal emergence, and 100 denoting nonermegence or complete destruction of at least the visible plant parts.

EXPERIMENTS IN THE OPEN

The experiments were carried out on small plots with loamy sand (pH 6), the humus content being from 1 to 1.5%. In the preemergence treatment, the compounds were applied either immediately after the crop plants had been sown or up to 3 days thereafter. The crop plants were sown in rows. The weed flora was natural. The substances were emulsified or dispersed in water as vehicle, and applied by means of a motor-driven plot spray mounted on a hitch. The amount of compounds of the formula I which was applied varied from compound to compound and was between 0.25 and 2.0 kg/ha.

The comparative agents employed were product A (used in the greenhouse experiments) at 0.25, 0.5 and 1.0 kg/ha, and the herbicide of the formula

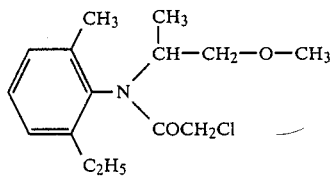

(B; German Laid Open Application DE-OS No. 2,328,340) applied at a rate of 2.0 kg/ha.

Where no rain fell, artificial irrigation was carried out to ensure germination and growth of the crop plants and weeds. All the experiments were run for several months. During this period, assessments on the 0 to 100 scale were made at certain intervals.

The plants species used in the experiments were *Alopecurus myosuroides, Avena fatua, Beta vulgaris, Brassica napus, Bromus tectorum, Chenopodium album, Echinochloa crus-galli,* Galinsoga spp., *Glycine max., Gossypim hirsutum, Sorghum halepense, Stellaria media, Zea mays,* Matricaria spp., and Lamium spp.

In investigations into the herbicidal action on preemergence application in the greenhouse of 1.0 kg/ha, for instance compound No. 18 was tolerated particularly well—and much better than prior art compound A—by certain broadleaved crop plants. With regard to their herbicidal action on unwanted grasses, both active ingredients were similar.

In experiments in the open, for instance compound no. 2, applied preemergence at rates of 0.25 and 1.0 kg/ha, was better tolerated than herbicide A and had an improved herbicidal action on *Echinochloa grus-galli*.

Compound no. 2, applied preemergence in the open at a rate of 2.0 kg/ha, had a better herbicidal action than comparative agent B on various unwanted broadleaved plants and at the same time was tolerated to a high degree by soybeans.

Compound no. 5, applied preemergence in the open at a rate of for instance 0.5 kg/ha, had a herbicidal action superior to that of comparative agent A and was well tolerated by the crop plant Indian corn.

To increase the spectrum of action and to achieve synergistic effects, the compounds of the formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the compounds of the formula I, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Nonphytotoxic oils and oil concentrates may also be added.

We claim:

1. A substituted N-aminomethylhaloacetanilide of the formula

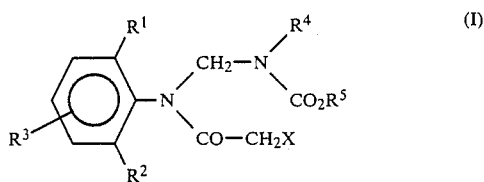

where $R^1$ and $R^2$ are each $C_1$-$C_2$-alkyl, $R^3$ is hydrogen or $C_1$-$C_4$-alkyl, $R^4$ is —CO—NH$_2$, $R^5$ is $C_1$-$C_6$-alkyl and X is halogen.

2. An N-aminomethylhaloacetanilide of the formula I as set forth in claim 1, where X is chlorine.

3. A herbicidal agent containing inert additives and an N-aminomethylhaloacetanilide of the formula

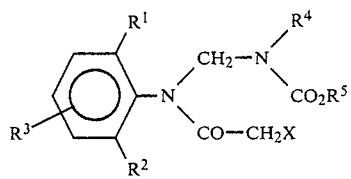

where $R^1$ and $R^2$ are each $C_1$-$C_2$-alkyl, $R^3$ is hydrogen or $C_1$-$C_4$-alkyl, $R^4$ is —CO—NH$_2$, $R^5$ is $C_1$-$C_6$-alkyl and X is halogen.

4. A herbicidal agent as set forth in claim 3, containing an N-aminomethylhaloacetanilide of the formula I, where X is chlorine.

5. A process for combatting unwanted plant growth, wherein the plants and/or their location are treated with a herbicidally effective amount of an N-aminomethylhaloacetanilide of the formula I as set forth in claim 1.

6. An N-aminomethylhaloacetanilide of the formula I as set forth in claim 2, where $R^3$ is hydrogen.

* * * * *